(12) United States Patent
Glass et al.

(10) Patent No.: US 12,594,172 B2
(45) Date of Patent: Apr. 7, 2026

(54) SYSTEM AND METHOD FOR IMPLANTABLE MUSCLE INTERFACE

(71) Applicant: The Johns Hopkins University, Baltimore, MD (US)

(72) Inventors: Connor Glass, Baltimore, MD (US); Nitish V. Thakor, Baltimore, MD (US); Sami Tuffaha, Baltimore, MD (US); Alexis Lowe, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 660 days.

(21) Appl. No.: 17/926,507

(22) PCT Filed: May 25, 2021

(86) PCT No.: PCT/US2021/034095
§ 371 (c)(1),
(2) Date: Nov. 18, 2022

(87) PCT Pub. No.: WO2021/242775
PCT Pub. Date: Dec. 2, 2021

(65) Prior Publication Data
US 2023/0181340 A1 Jun. 15, 2023

Related U.S. Application Data

(60) Provisional application No. 63/030,778, filed on May 27, 2020.

(51) Int. Cl.
*A61F 2/72* (2006.01)
*A61B 5/00* (2006.01)
(Continued)

(52) U.S. Cl.
CPC .............. *A61F 2/72* (2013.01); *A61B 5/0031* (2013.01); *A61B 5/313* (2021.01); *A61B 5/389* (2021.01); *A61F 2002/705* (2013.01)

(58) Field of Classification Search
CPC ........ A61F 2/72; A61F 2002/705; A61F 2/54; A61F 2/60; A61F 2002/5061; A61F 5/01;
(Continued)

(56) References Cited

U.S. PATENT DOCUMENTS

| | | | |
|---|---|---|---|
| 2012/0188158 A1* | 7/2012 | Tan .......................... | G06F 3/015 345/156 |
| 2013/0090706 A1* | 4/2013 | Nudo ................. | A61N 1/36139 607/62 |

(Continued)

FOREIGN PATENT DOCUMENTS

| | | |
|---|---|---|
| CN | 1545988 A | 11/2004 |
| CN | 103655011 A | 3/2014 |

(Continued)

OTHER PUBLICATIONS

International Preliminary Report on Patentability in International Application No. PCT/US2021/034095, mailed on Dec. 8, 2022, 6 pages.

(Continued)

*Primary Examiner* — Nitin Patel
(74) *Attorney, Agent, or Firm* — Fish & Richardson P.C.

(57) ABSTRACT

An implantable human-machine interfacing system is disclosed that includes an implantable muscle interface device including a substrate including a first plurality of sensors and a second plurality of amplifiers that capture and amplify, respectively, electromyographic (EMG) signals arising from motor units under control of neural signals representative of volitional limb movements; and a transceiver device connected to the first plurality of sensors that wirelessly transmits signals to an external decoder that produces decoded signals that discriminate motor signals representative of movements of the motor units, wherein the substrate at least partially surrounds a muscle from which the EMG signals arise; and a receiver device that uses the decoded signals for (Continued)

interaction with an external system. The system includes a first plurality of electrodes and a second implantable power source that imparts electrical stimulation to the underlying tissues and sensory axons within for the purposes of sensory feedback and neuromodulation.

13 Claims, 18 Drawing Sheets

(51) Int. Cl.
    *A61B 5/313*           (2021.01)
    *A61B 5/389*           (2021.01)
    *A61F 2/70*            (2006.01)
(58) Field of Classification Search
    CPC ....... A61B 5/0031; A61B 5/313; A61B 5/389;
                    A61B 5/686; A61B 5/296; A61N
                    1/36103; A61N 1/36135
    See application file for complete search history.

(56) References Cited

U.S. PATENT DOCUMENTS

| | | | |
|---|---|---|---|
| 2013/0304174 A1 | 11/2013 | Langhals et al. | |
| 2013/0317648 A1* | 11/2013 | Assad ..................... | G06F 3/011 |
| | | | 700/258 |
| 2014/0088379 A1 | 3/2014 | Irazoqui et al. | |
| 2015/0173918 A1 | 6/2015 | Herr et al. | |
| 2016/0143751 A1* | 5/2016 | Chestek ................... | A61F 2/72 |
| | | | 623/25 |
| 2016/0346099 A1 | 12/2016 | Herr et al. | |
| 2018/0043167 A1 | 2/2018 | Gaddam et al. | |
| 2019/0231204 A1* | 8/2019 | Heydari ............... | A61B 5/6868 |
| 2019/0247650 A1 | 8/2019 | Tran | |
| 2020/0406035 A1* | 12/2020 | Sharma ................... | A61B 5/11 |
| 2021/0259859 A1* | 8/2021 | Farina ...................... | A61F 2/72 |
| 2022/0022801 A1* | 1/2022 | Wendelken .......... | A61B 5/7246 |
| 2022/0253024 A1* | 8/2022 | Oxley ................. | A61B 5/7465 |

FOREIGN PATENT DOCUMENTS

| | | |
|---|---|---|
| CN | 110312471 A | 10/2019 |
| CN | 110337269 A | 10/2019 |
| CN | 210158741 U | 3/2020 |
| JP | 2002-028143 A | 1/2002 |
| JP | 2008-212652 A | 9/2008 |
| JP | 2010-259745 A | 11/2010 |
| WO | WO 2020036958 | 2/2020 |

OTHER PUBLICATIONS

International Search Report and Written Opinion in International Application No. PCT/US2021/034095, dated Aug. 26, 2021, 6 pages.
Extended Search Report in European Appln. No. 21811943.6, dated Jun. 4, 2024, 8 pages.
McDonnall et al., "Implantable multichannel wireless electromyography for prosthesis control," Proceedings of the 34th Annual International Conference of the IEEE EMBS, Aug. 28, 2012, 1350-1353.

* cited by examiner

EMG electronics unit
108, 110, 116

EMG
acquisition unit

EMG

FRONT

Nerve - to
innervate muscle
710

102

Blood vessel to
vascularize muscle
708

702
Muscle

1402

1406  1408

1410

1404

1412

1414

1414

1416

FLEX COMPARTMENT

EXTENSOR COMPARTMENT

CROSS SECTIONAL VIEW OF FOREARM

SIDE 1

TOP

BOTTOM

SYSTEM AND METHOD FOR IMPLANTABLE MUSCLE INTERFACE

CROSS-REFERENCE TO RELATED APPLICATIONS

This application is a National Stage application under 35 U.S.C. § 371 of International Application No. PCT/US2021/034095 having an International Filing Date of May 25, 2021, which claims priority to U.S. provisional patent application No. 63/030,778 filed on May 27, 2020, which are hereby incorporated by reference in their entirety.

FIELD

The present teachings generally relate a system and method for implantable muscle interface.

BACKGROUND

Amputation is still considered a measure of last resort for many who have lost limb functionality from nerve damage because prosthetic functionality has remained relatively static over the past forty or more years. This is partially due to the lack of a strong link between machines and the human nervous system. Because humans lack a meaningful way to seamlessly communicate with machines, this continues to represent a bottleneck for advancements in prosthetic and exoskeleton assistive technology as well as future implications of such technology.

SUMMARY

In accordance with examples of the present disclosure, an implantable muscle interface system is disclosed. The implantable muscle interface system comprises a substrate comprising: a first plurality of sensors and a second plurality of amplifiers that capture and amplify, respectively, electromyographic (EMG) signals arising from motor units under control of neural signals representative of volitional limb movements; and a wireless transceiver device electrically connected to the first plurality of sensors that wirelessly transmits signals to an external decoder that produces decoded signals that discriminate motor signals representative of movements of the motor units, wherein the substrate at least partially surrounds a muscle from which the EMG signals arise; and a receiver device that uses the decoded signals for interaction with an external system.

Various additional features can be included in the implantable muscle interface system including one or more of the following features. The substrate is flexible, rigid, or semi-rigid. The receiver device comprises amplifying components, filtering components, wireless communication components, or combinations thereof. The substrate, the first plurality of sensors, the second plurality of amplifiers, and the wireless transceiver device are enclosed in a single hermetically sealed container or encapsulated coating. The implantable muscle interface system can further comprise a power source that powers the first plurality of sensors, the second plurality of amplifiers, and the wireless transceiver device. The substrate, the first plurality of sensors, the second plurality of amplifiers, the wireless transceiver device, and the power source are enclosed in a single hermetically sealed container or encapsulated coating. The first plurality of sensors, the second plurality of amplifiers, and the wireless transceiver device are externally powered by an electromagnetic, ultrasonic, piezoelectric, or optical power source. The signals transmitted by the wireless transceiver device are analog signals that are multiplexed from multiple channels from the first plurality of sensors or analog signals that are multiplexed from multiple channels from the first plurality of sensors and digitized with analog-to-digital converters, or encrypted signals for secure communication. The substrate is composed of a biocompatible material comprising polymers, parylene, plastics, rubbers, silicone, polymeric fiber, silk fibroin, 3D printing polymers, polyimide, Polydimethylsiloxane (PDMS), metals, hydrogels, or acellular scaffolds. The substrate is composed of biocompatible polymers with conductive electrodes and conductive traces deposited or embedded therein, comprising biocompatible metals, conductive polymers, electrically conductive carbon-based materials comprising fibers, nanotubes, and graphene, gold, platinum, polypyrrole, Poly(3,4-ethylenedioxythiophene) (PEDOT), poly(3,4-ethylenedioxythiophene) polystyrene sulfonate (PEDOT:PSS), or combinations thereof. The external system comprises a prosthetic limb, an orthosis, an exoskeleton, a computer, a home appliance, a remote controller, a gaming device, a mobile computing device, an audio device, an augmented reality system, a virtually reality system, or a human augmentation/enhancement device. The implantable muscle interface device is compatible with target tissue comprising muscles in various biological states including unaltered, vascularized-innervated, vascularized-denervated, devascularized-denervated, devascularized-innervated muscle, or muscle graft including autograft, xenograft, allograft, isograft, cell culture, or a synthetic alternative. The substrate comprises a first plurality of electrodes (such as one or more stimulating electrodes) or ultrasonic transducers that provide electrical or ultrasonic stimulation to underlying sensory axons for sensory feedback from prosthetic limbs or exoskeletons.

In accordance with examples of the present disclosure, a method of controlling an external device using an implantable muscle interface device is disclosed. The method comprises obtaining signals from one or more sensors that detect electromyography (EMG) signals representative of excitation or contraction of underlying muscles, wherein the one or more sensors are deposited or embedded within a substrate that at least partially surrounds the underlying muscles; and detecting the EMG signals with amplifier and filter electronics transmitting the EMG signals wirelessly by an implanted transceiver; transmitting the EMG signals wirelessly by an implanted transceiver; receiving the EMG signals wirelessly by an external receiver; decoding the EMG signals that were detected using a decoding algorithm that converts the EMG signals into discrete control signals; and using the control signals that are separated for manipulation of devices based on machine learning algorithms which correlate the control signals to an intent of a user.

Various additional features can be included in the implantable muscle interface system including one or more of the following features. The substrate is composed of biocompatible materials comprising polymers, plastics, rubbers, silicone, polymeric fiber, silk fibroin, 3D printing polymers, polyimide, Polydimethylsiloxane (PDMS), metals, hydrogels, or acellular scaffolds. The substrate is composed of biocompatible polymers with conductive electrodes and conductive traces deposited or embedded therein, comprising biocompatible metals, conductive polymers, electrically conductive carbon-based materials comprising fibers, nanotubes, and graphene, gold, platinum, polypyrrole, Poly(3,4-ethylenedioxythiophene) (PEDOT), or combinations thereof. The external system comprises a prosthetic limb, an orthosis, an exoskeleton, a computer, a home appliance, a remote controller, a gaming device, a mobile computing device, an audio device, an augmented reality system, a virtually reality system, or a human augmentation/enhancement device. The implantable muscle interface device is compatible with target tissue comprising muscles in various biological states including unaltered, vascularized-innervated, vascularized-denervated, devascularized-denervated, devascularized-innervated muscle, or muscle graft including autograft, xenograft, allograft, isograft, cell culture, or a synthetic alternative.

In accordance with examples of the present disclosure, a method of installing an implantable muscle interface device is disclosed. The method of installing the implantable muscle interface devices comprises preparing an implantation site; and securing a substrate to the implantation site, wherein the substrate comprising one or more sensors that detect electromyography (EMG) signals representative of movements of underlying muscles, wherein the substrate at least partially surrounds the underlying muscles. The preparing of the implantation site comprises elevating at least a muscle segment of the underlying muscles from surrounding tissues while remaining attached to blood vessels that provide perfusion; identifying nerves supplying the at least the muscle segment with electrical stimulation using one or more stimulating electrodes or one or more ultrasonic transducers; dividing at least muscle segment that is identified to ensure denervation; wrapping a distal end of a proximal stump of a transected nerve or nerve fascicle with at least the muscle segment that is isolated or placing the distal end of the proximal stump of the transected nerve within a portion of the muscle segment and securing the proximal stump with a suture or with fibrin glue.

BRIEF DESCRIPTION OF THE DRAWINGS

The accompanying drawings, which are incorporated in, and constitute a part of this specification, illustrate implementations of the present teachings and, together with the description, serve to explain the principles of the disclosure. In the figures.

It should be noted that some details of the figures have been simplified and are drawn to facilitate understanding of the present teachings rather than to maintain strict structural accuracy, detail, and scale.

DETAILED DESCRIPTION

Generally speaking, the present disclosure provides for an implantable muscle interface system, a method of controlling an external device using an implantable muscle interface device, and a method of installing an implantable muscle interface device. In some examples, the implantable muscle interface device can be assembled from its component system of electrodes or ultrasonic transducers, electronics, wireless, and other examples 3D printed and can be configured as a cuff-like muscle interface that interacts with newly innervated sections of muscle following nerve transection and is capable of both recording (by one or more sensors such as recording electrodes) from and stimulating (by one or more stimulating electrodes or one or more ultrasonic transducers) the muscles and influencing the neural activity in the peripheral nervous system and controlling the performance of the prostheses. The implantable muscle interface device can be used to harness EMG signals that result from a surgical invention used to treat/prevent nerve pain following the severing of a nerve, such as a single-nerve injury or complete limb amputation. The implantable muscle interface device can then be used through the captured EMG signals to control machines or devices such as, but not limited to, prosthetic limbs, exoskeletons, or other assistive or mobility devices such as motorized wheelchairs. As used herein, the term "sensor" can be an recording electrode.

Figures 1A, 1B, 1C, 1D, 1E:
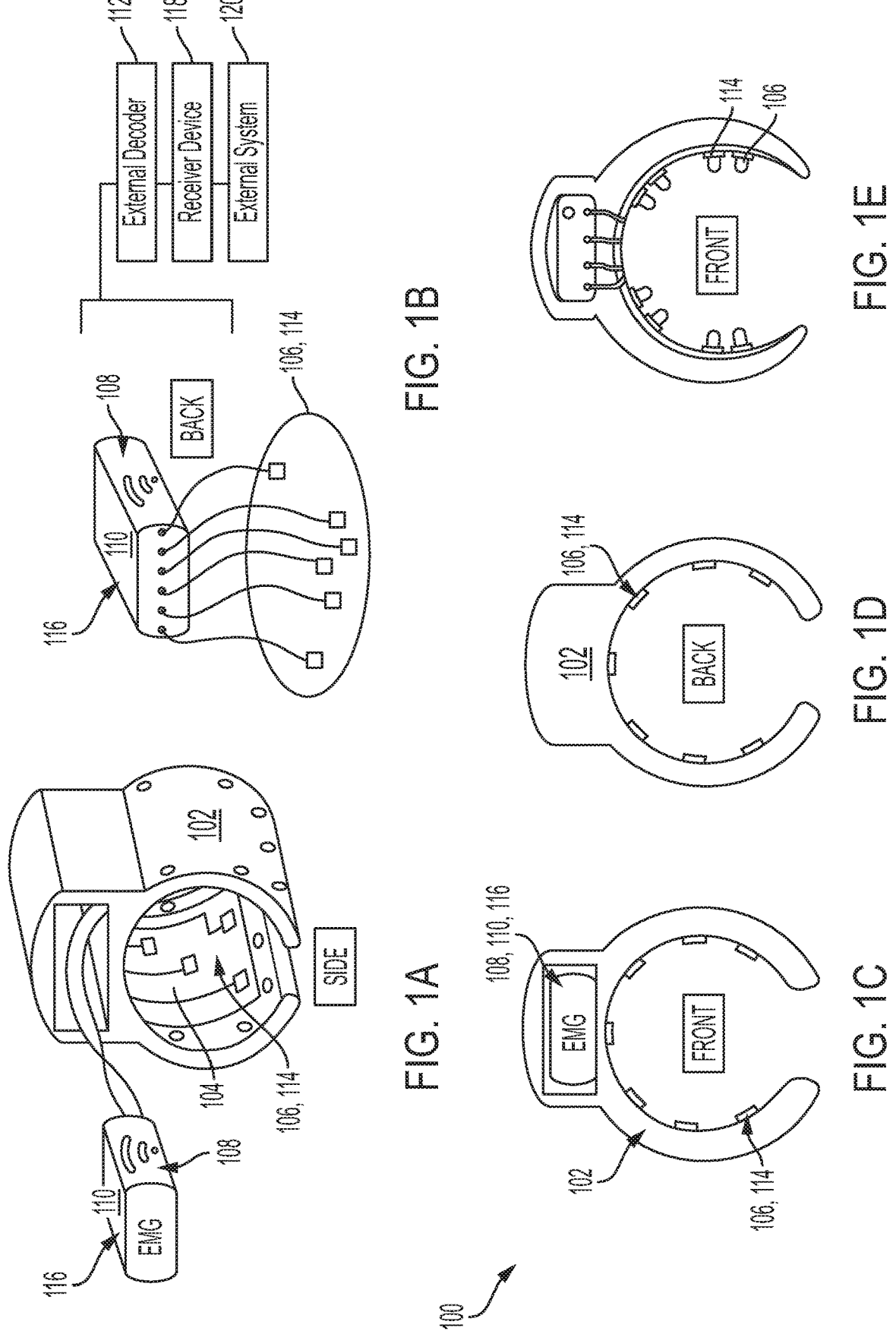
FIG. 1A shows a perspective view of a first example implantable muscle interface system according to examples of the present disclosure.
FIG. 1B shows a detailed view of a portion of FIG. 1A.
FIG. 1C shows a front view of the system of FIG. 1A.
FIG. 1D shows a front view of the system of FIG. 1A.
FIG. 1E shows another front view of the system of FIG. 1A.
Figures 2A, 2B, 2C, 2D:
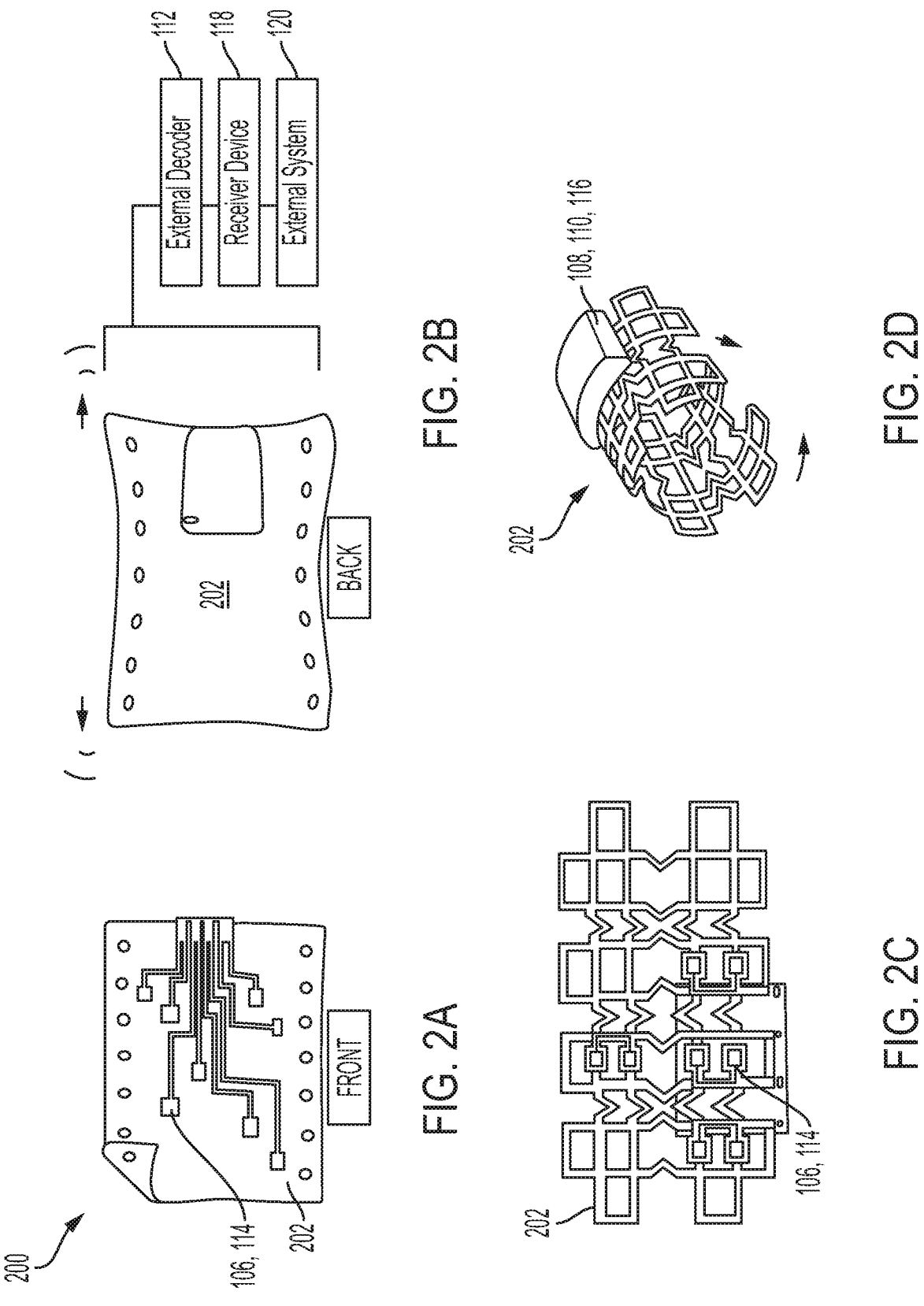
FIG. 2A shows a front view of a second and third example implantable muscle interface system according to examples of the present disclosure.
FIG. 2B shows a back view of the system of FIG. 2A.
FIG. 2C. shows a detailed view of the system of FIG. 2A.
FIG. 2D shows another view of the system of FIG. 2A.

FIG. 1A shows a perspective view of a first example implantable muscle interface system 100 according to examples of the present disclosure. FIG. 1B shows a detailed view of a portion of FIG. 1A. FIG. 1C shows a front view of the system of FIG. 1A. FIG. 1D shows a front view of the system of FIG. 1A. FIG. 1E shows another front view of the system of FIG. 1A. FIG. 2A shows a front view of a second and third example implantable muscle interface system 200 according to examples of the present disclosure. FIG. 2B shows a back view of the system of FIG. 2A. FIG. 2C shows a detailed view of the system of FIG. 2A. FIG. 2D shows another view of the system of FIG. 2A. Implantable muscle interface systems 100 and 200 comprise implantable muscle interface device 102. Implantable muscle interface device 102 is compatible with target tissue comprising muscles in various biological states including vascularized-innervated, vascularized-denervated, devascularized-denervated, devascularized-innervated muscle, or muscle graft including autograft, xenograft, allograft, isograft, cell culture, or a synthetic alternative.

Implantable muscle interface device 102 comprises first substrate 104 or second substrate 202. First substrate 104 and second substrate 202 can be flexible, rigid, or semi-rigid. First substrate 104 is rigid and second substrate 202 is flexible. In some examples, first substrate 104 and/or second substrate 202 is composed of a biocompatible material comprising polymers, plastics, rubbers, silicone, polymeric fiber, silk fibroin, 3D printing polymers, polyimide, Polydimethylsiloxane (PDMS), metals, hydrogels, acellular scaffolds or combinations thereof. In some examples, first substrate 104 and/or second substrate 202 is composed of biocompatible polymers with conductive electrodes or ultrasonic transducers and conductive traces deposited or embedded therein, comprising biocompatible metals, conductive polymers, electrically conductive carbon-based materials comprising fibers, nanotubes, and graphene, gold, platinum, polypyrrole, Poly(3,4-ethylenedioxythiophene) (PEDOT), poly(3,4-ethylenedioxythiophene) polystyrene sulfonate (PEDOT:PSS), other conductive polymers, or combinations thereof.

First substrate 104 and/or second substrate 202 comprise a first plurality of sensors 106 and a first plurality of amplifiers 108. First plurality of sensors 106 capture and first plurality of amplifiers 108 amplify electromyographic (EMG) signals arising from motor units under control of neural signals representative of volitional limb movements. Implantable muscle interface device 102 also comprises a wireless transceiver device 110 that is electrically connected to first plurality of sensors 106 that wirelessly transmits signals to an external decoder 112 that produces decoded signals that discriminate motor signals representative of movements of the motor units. First substrate 104 and/or second substrate 202 at least partially surround a muscle from which the EMG signals arise. In some examples, first substrate 104 and/or second substrate 202, first plurality of sensors 106, first plurality of amplifiers 108, and wireless transceiver device 110 are enclosed in a single hermetically sealed container. The hermetically sealed container will completely enclose all components of the interface device that are not designed for interacting with tissue, such as the substrate and sensors which may be partially enclosed, and shall comprise some biocompatible material such as, but not limited to, titanium, alumina, zirconia, or other ceramics. In some examples, first substrate 104 and/or second substrate 202 can comprise the first plurality of electrodes 114 (or ultrasonic transducers) that provide electrical stimulation (by one or more stimulating electrodes) (or ultrasonic stimulation by one or more ultrasonic transducers) to underlying sensory axons for sensory feedback from prosthetic limbs.

Figure 3:
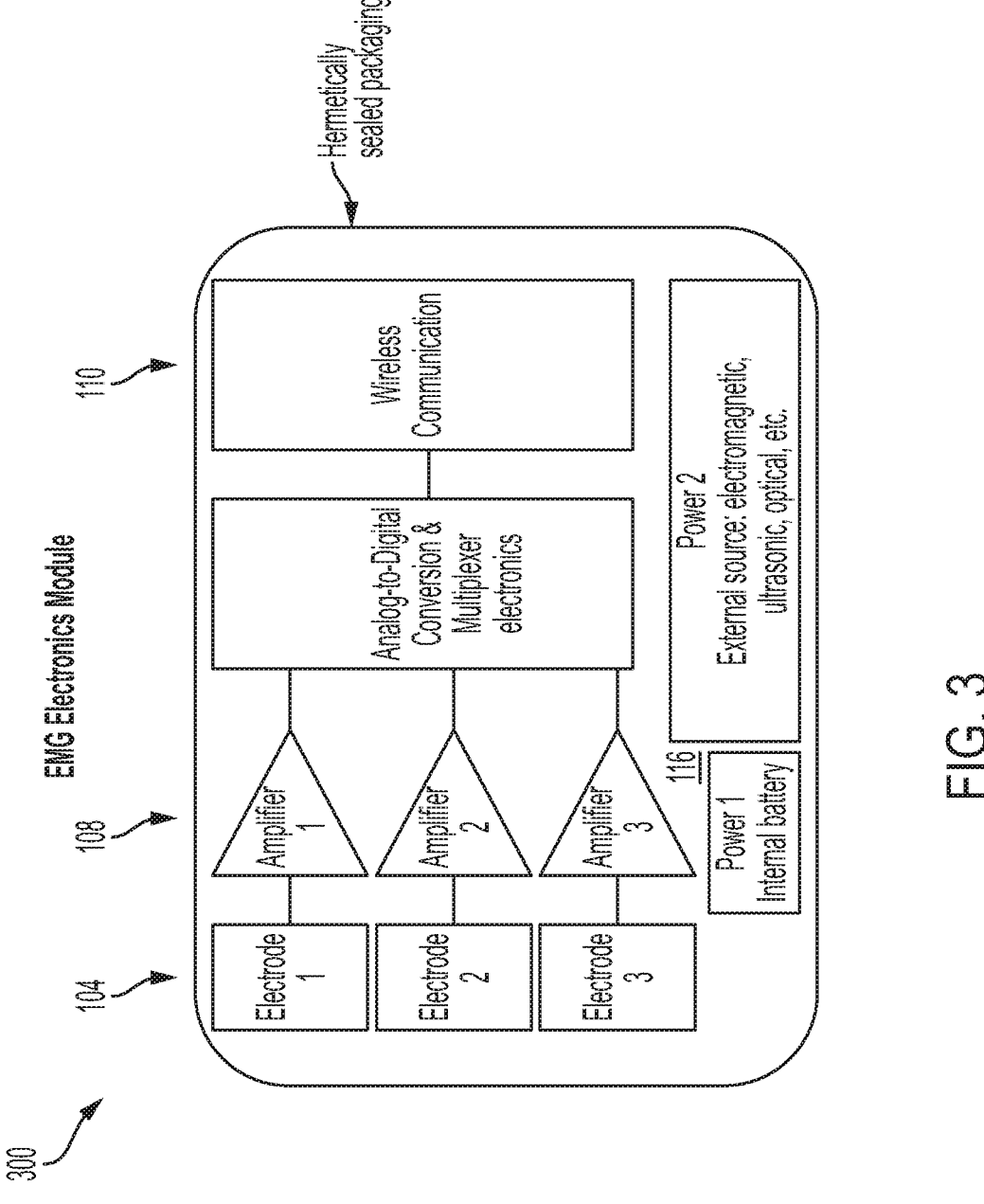
FIG. 3 shows an example of the electronic components within the implantable muscle interface system according to examples of the present disclosure.

In some examples, implantable muscle interface device 102 comprises a power source 116 that powers one or more of the first plurality of sensors 106, first plurality of amplifiers 108, wireless transceiver device 110, or the first plurality of electrodes 114. In some examples, one or more of the first plurality of sensors 106, first plurality of amplifiers 108, wireless transceiver device 110, or the first plurality of electrodes 114 are externally powered by an electromagnetic, ultrasonic, piezoelectric, or optical power source. FIG. 3 shows an example layout 300 for all of these electronic components. The signals transmitted by wireless transceiver device 110 can be analog signals that are multiplexed from multiple channels from the first plurality of sensors or analog signals that are multiplexed from multiple channels from the first plurality of sensors and digitized with analog-to-digital converters, or encrypted signals for secure communication.

Implantable muscle interface system 100 also comprises a receiver device 118 that uses the decoded signals for interaction with external system 120. Receiver device 118 can comprise amplifying components, filtering components, or both.

In some examples, external system 120 comprises a prosthetic limb, a wheelchair, a computer, a mouse cursor, a home appliance, a remote controller, a gaming device, a mobile computing device, an audio device, an augmented reality system, a virtually reality system, or a human augmentation/enhancement device.

Figure 4:
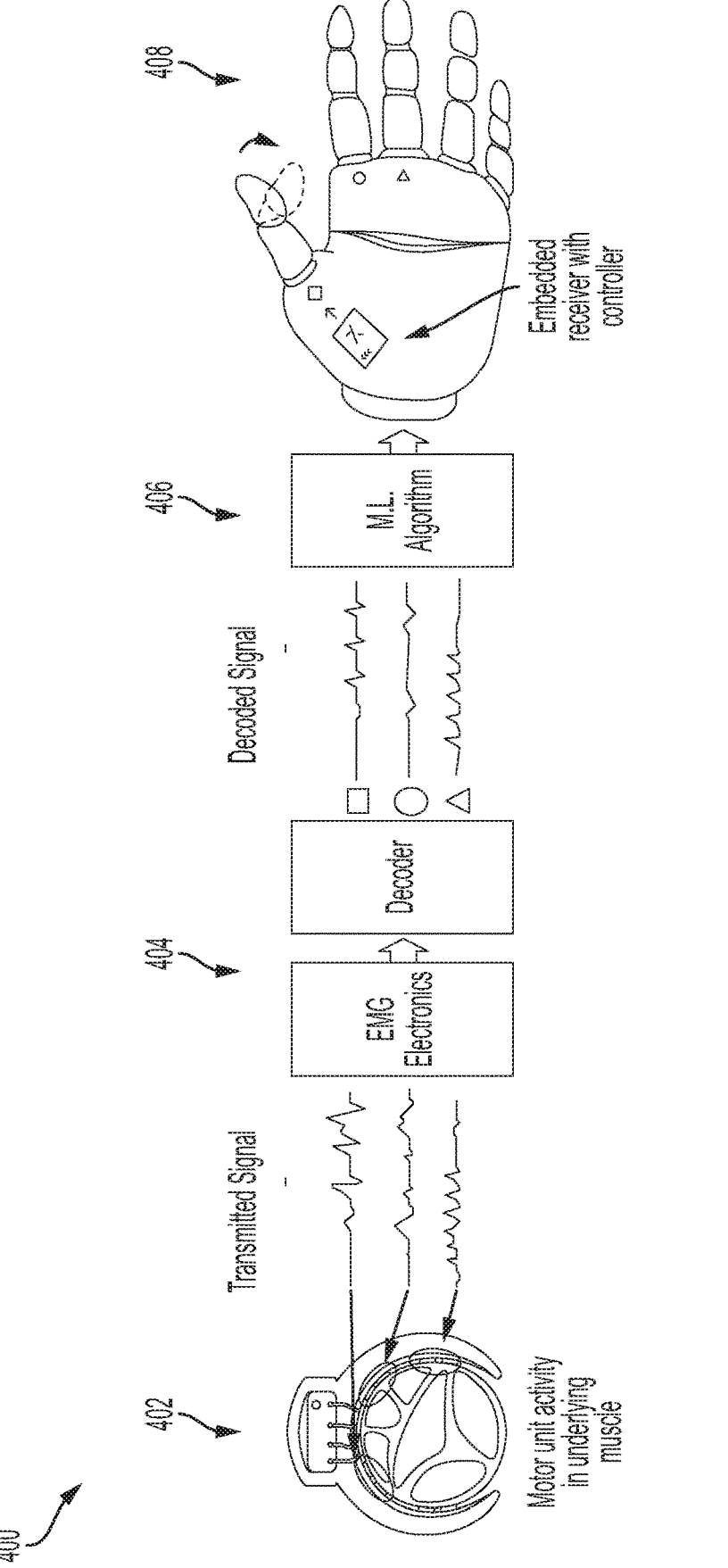
FIG. 4 shows a method of transmitting signals to and from an external device using an implantable muscle interface device according to examples of the present disclosure.

FIG. 4 shows a method 400 of controlling an external device using an implantable muscle interface device according to examples of the present disclosure. Method 300 begins by obtaining signals from one or more sensors that detect electromyography (EMG) signals representative of excitation or contraction of underlying muscle, as in 402. Referring back to FIGS. 1 and 2, the one or more sensors, such as first plurality of sensors 106, are deposited on, embedded within, or attached to a substrate, such as first substrate 102 or second substrate 202, and that at least partially surrounds the underlying muscles. First substrate 102 and second substrate 202 of implantable muscle interface device 102 can be composed of biocompatible materials comprising polymers, plastics, rubbers, silicone, polyimide, perylene, polymeric fiber, silk fibroin, 3D printing polymers, polyimide, Polydimethylsiloxane (PDMS), metals, hydrogels, acellular scaffolds or combinations thereof. First substrate 102 and second substrate 202 can be composed of biocompatible polymers with conductive electrodes and conductive traces deposited or embedded therein, comprising biocompatible metals, conductive polymers, electrically conductive carbon-based materials comprising fibers, nanotubes, and graphene, gold, platinum, polypyrrole, Poly(3,4-ethylenedioxythiophene) (PEDOT), or combinations thereof. Implantable muscle interface device 102 can be compatible with target tissue comprising muscles in various biological states including vascularized-innervated, vascularized-denervated, devascularized-denervated, devascularized-innervated muscle, or muscle graft including autograft, xenograft, allograft, isograft, cell culture, or a synthetic alternative.

Method 400 continues by detecting the EMG signals with amplifier and filter electronics transmitting the EMG signals wirelessly by an implanted transceiver, as in 404. Continuing with the example with regard to FIGS. 1 and 2, EMG signals are detected by the first plurality of sensors 106 and amplified by the first plurality of amplifiers 108. Method 400 continues by receiving the EMG signals wirelessly by an external receiver, as in 404. Continuing with the example, wireless transceiver device 110 receives the EMG signals and wirelessly transmits them to receiver device 118. Method 400 continues by decoding the EMG signals that were detected using a decoding algorithm that converts the EMG signals into discrete control signals, as in 406. Method 400 continues by using the control signals that are separated for manipulation of devices based on machine learning algorithms which correlate the plurality of control signals to the intent of a user, as in 408. For example, the devices can comprise a prosthetic limb, a wheelchair, a computer, a mouse cursor, a home appliance, a remote controller, a gaming device, a mobile computing device, an audio device, an augmented reality system, a virtually reality system, or a human augmentation/enhancement device.

Figure 5:
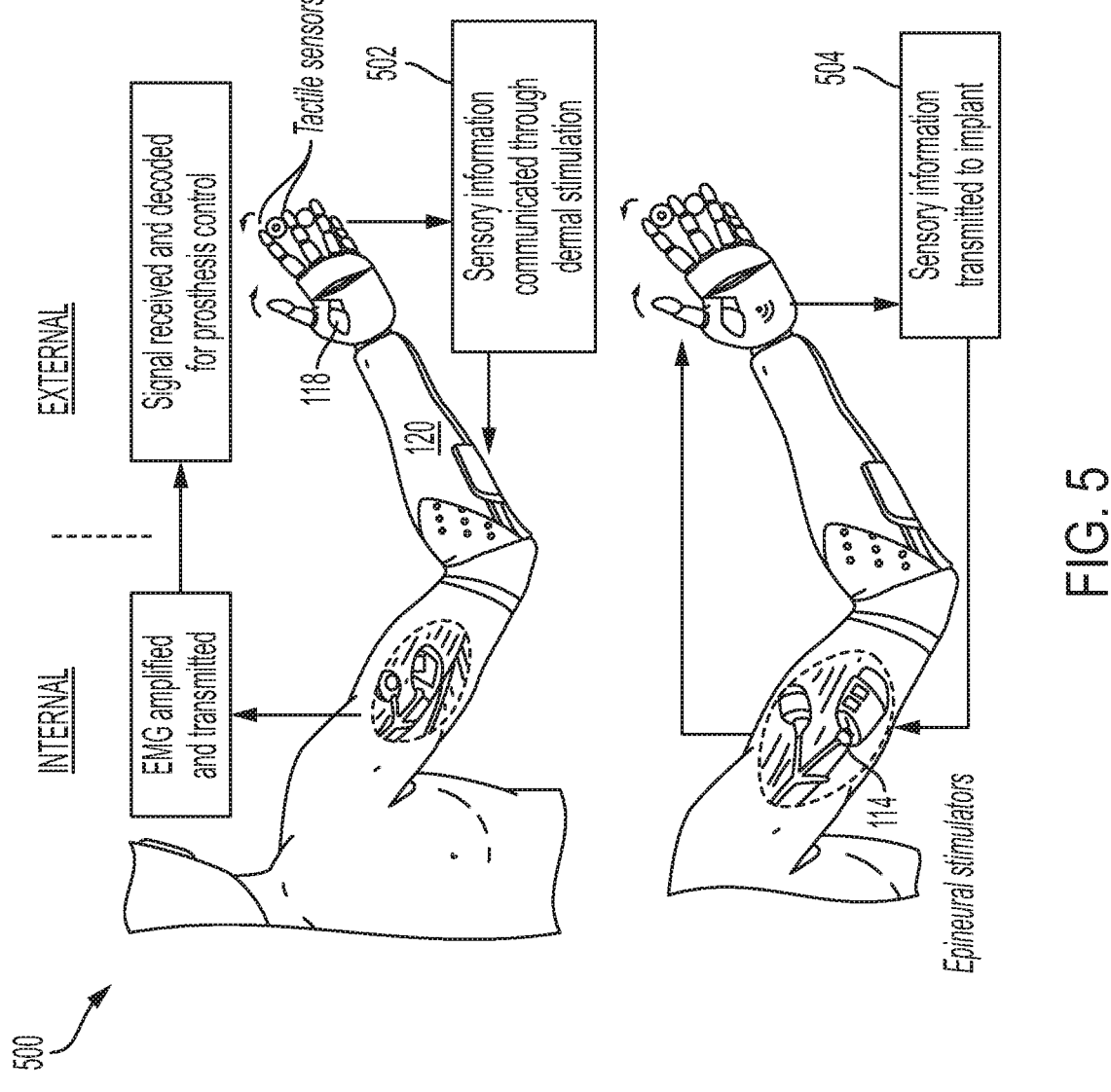
FIG. 5 shows a method of controlling an external device through decomposition of transmitted signals from an implantable muscle interface device according to examples of the present disclosure.

FIG. 5 shows a method 500 for using the implantable muscle interface system to control such an external device. In this example, transmitted EMG signals as a result of neuronal activity of the brachial plexus in an upper-limb amputee are received by a receiver device 118 within a prosthetic arm. The signals are decoded to electronically reposition the hand. This method 500 can be a one-way, forward control system, such as in 502. Alternative, method 500 can be a two-way communication system with sensory feedback, such as in 504. In a two-way system, the implantable muscle interface device 102 has both a wireless transceiver 110 and a receiver for receiving signals from external sensors. These signals are encoded in the form of electrical stimulation and delivered to the nervous system through the first plurality of stimulating electrodes 114 or one or more ultrasonic transducers.

Figure 6:
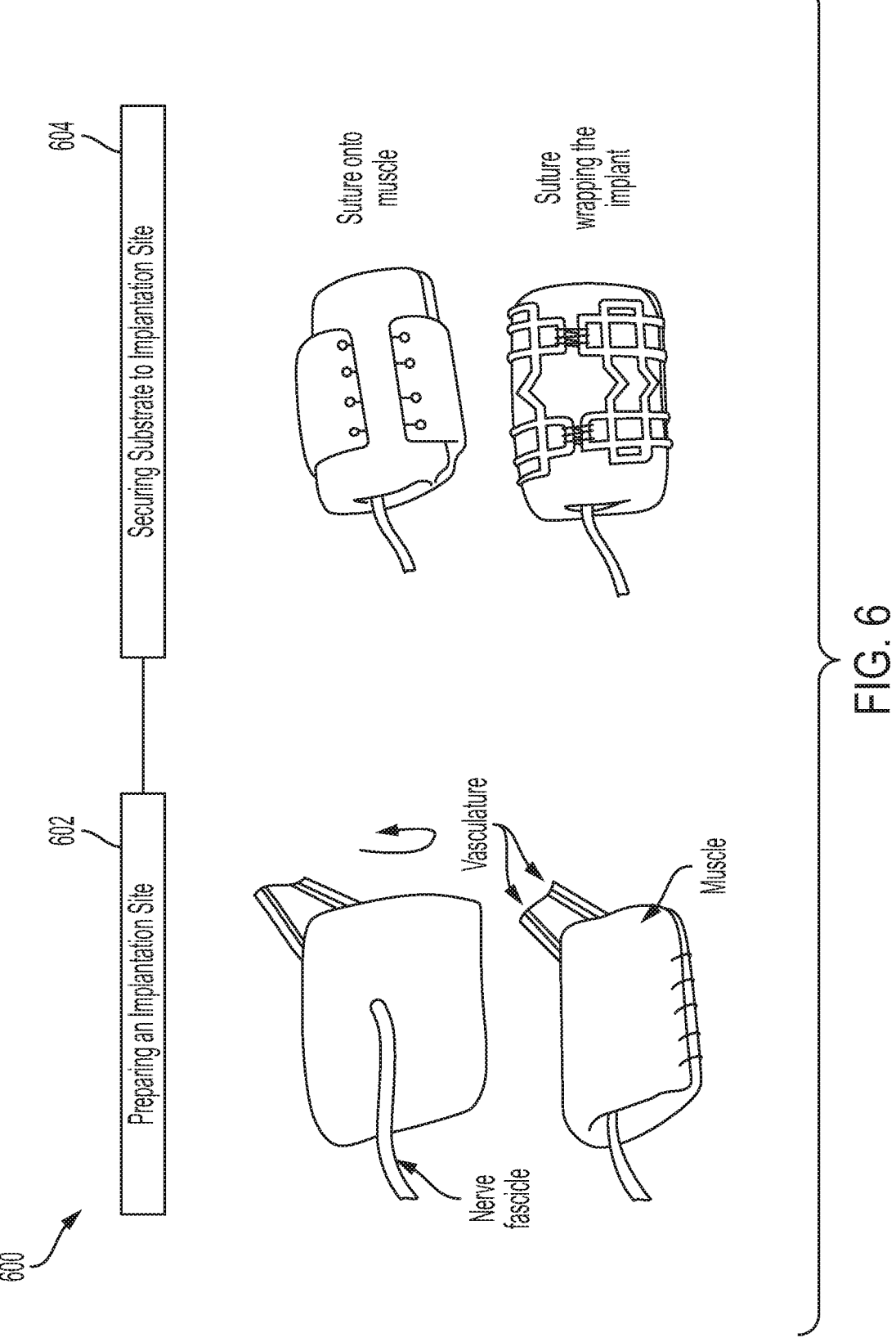
FIG. 6 shows a method of installing an implantable muscle interface device according to examples of the present disclosure.

FIG. 6 shows a method 600 of installing an implantable muscle interface device according to examples of the present disclosure. Method 600 begins by preparing an implantation site, as in 602. For example, preparing the implantation site comprises elevating at least a muscle segment of the underlying muscles from surrounding tissues while remaining attached to blood vessels that provide perfusion; identifying nerves supplying the at least the muscle segment with electrical stimulation; dividing the identified muscle segment to ensure denervation; wrapping a distal end of the proximal stump of a transected nerve or nerve fascicle with at least the muscle segment or placing the distal end of the proximal stump of the transected nerve within a portion of the muscle and securing the stump with a suture or with fibrin glue.

Method 600 continues by securing a substrate to the implantation site, as in 604. The device, with incorporated suture holes, is affixed to the tissue of interest and surrounding tissue bed via at least two sutures 180 degrees from each other on the proximal and distal ends of the device (at least 4 sutures in total). These sutures can be affixed to muscle, epineurium, perineurium, fascia, tendon, ligament, periosteum, etc. The attachment tissue and location will be dependent on each individual patient's anatomical requirements. The tissue/device construct may then be covered in some protective biodegradable sheathing to include but not limited to xenographic intestine, acellular wraps, synthetic wraps. This will be done to protect the device from fibrosis and tethering during the healing process. Referring again back to FIGS. 1 and 2, the substrate, such as first substrate 104 and second substrate 202, comprising one or more sensors, such as first plurality of sensors 106, that detect electromyography (EMG) signals representative of movements of underlying muscles. The substrate at least partially surrounds the underlying muscles. A wireless transceiver device, such as wireless transceiver device 110, is electrically connected to the one or more sensors and accompanying/interfacing electronics that wirelessly transmits the EMG signals to an external controller, such as receiver device 118 and/or external system 120.

Figure 7:
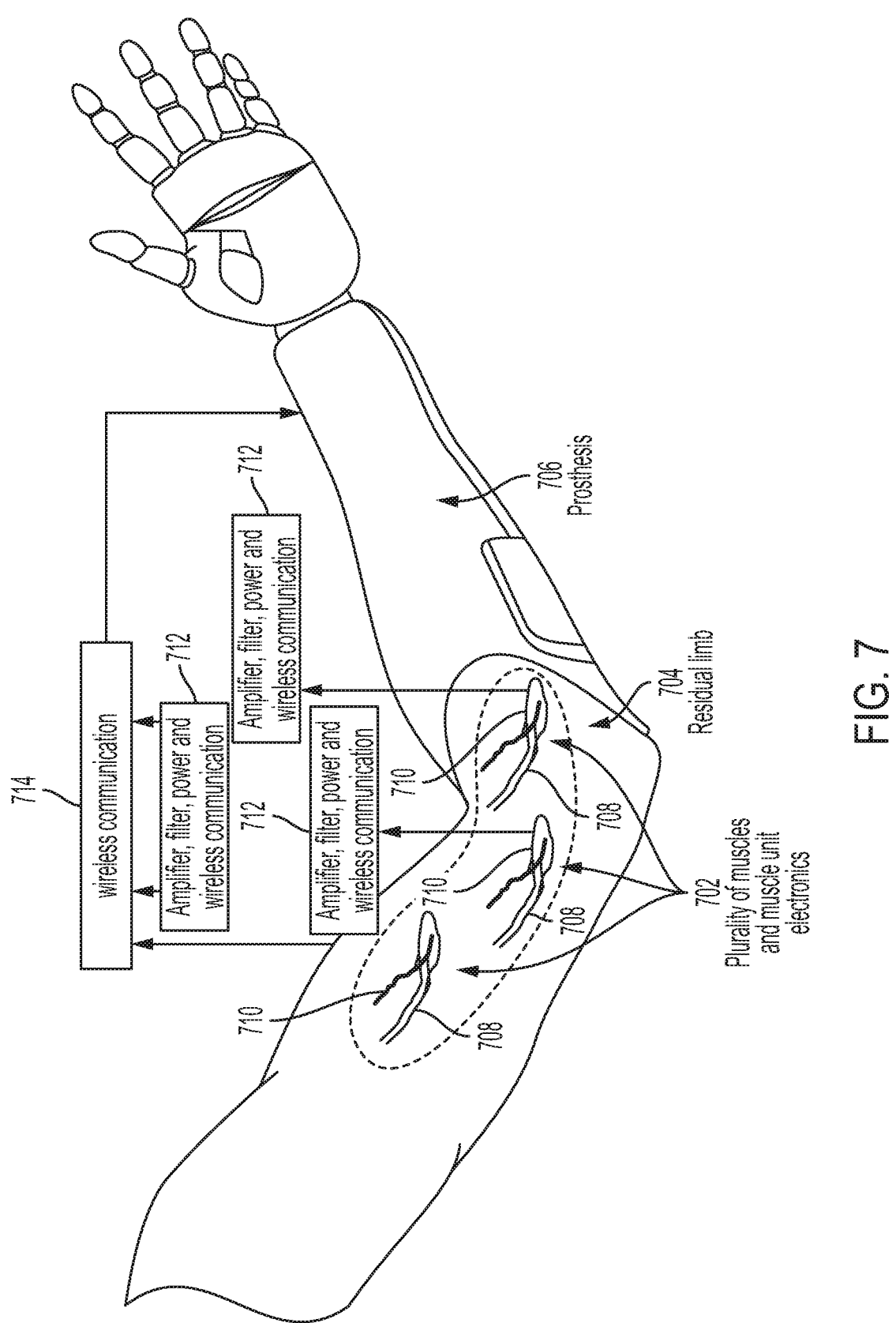
FIG. 7 shows a prosthesis controlled with a plurality of muscle unit according to examples of the present disclosure.

FIG. 7 shows a prosthesis controlled with a plurality of muscle units according to examples of the present disclosure. Three muscle units 702 are shown in residual limb 704 where each muscle unit includes a nerve 710 to innervate the muscle and a blood vessel 708 to vascularize the muscle. EMG signals are detected from each muscle unit using the device of FIG. 1 or 2 and are amplified, filtered, powered, and wirelessly communicated by associated electronics 712 using wireless communication module 714 to control prosthesis 706.

Figure 8:
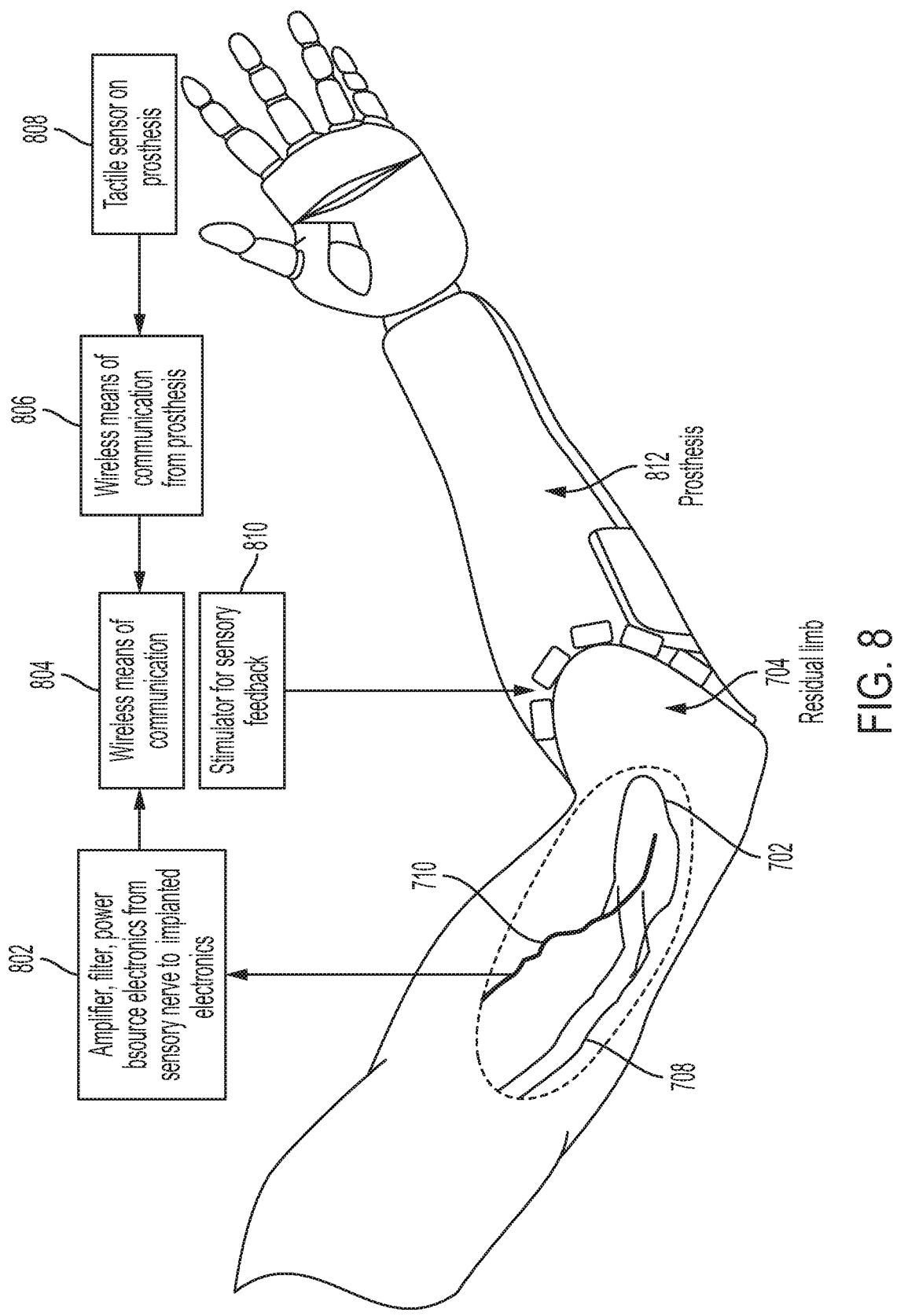
FIG. 8 shows a tactile sensor-enabled prosthesis controlled with a muscle unit according to examples of the present disclosure.

FIG. 8 shows a tactile sensor-enabled prosthesis controlled with a muscle unit according to examples of the present disclosure. Muscle unit 702 is shown in residual limb 704 where the muscle unit includes a nerve 710 to innervate the muscle and a blood vessel 708 to vascularize the muscle. EMG signals are detected from the muscle unit 702 using the device of FIG. 1 or 2 and are amplified, filtered, powered, and wirelessly communicated by associated electronics 802 using wireless communication module 804 to control tactile sensor-enabled prosthesis 812. Stimulating sensors 810 attached to the residual limb 704 provide sensory feedback for the user that is conveyed the tactile sensors 808 on the tactile sensor-enabled prosthesis 812 that are provided back at 806 to the device of FIG. 1 or 2 by wireless communication module 804.

Figure 9:
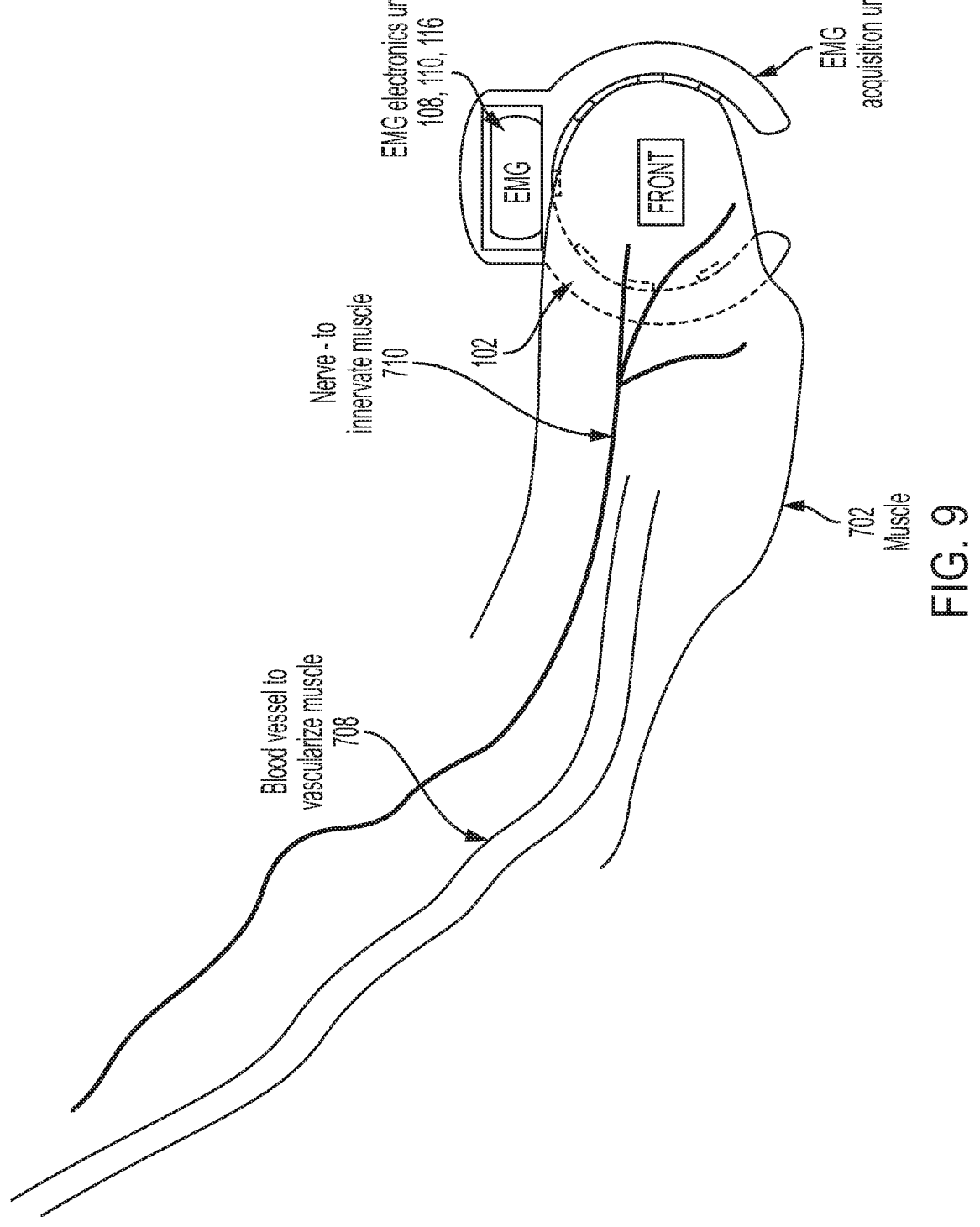
FIG. 9 shows attachment view of the device of FIG. 1 or FIG. 2 on a residual limb according to examples of the present disclosure.

FIG. 9 shows attachment view of the device of FIG. 1 or FIG. 2 on a residual limb according to examples of the present disclosure. Muscle unit 702 is shown in residual limb 704 where the muscle unit includes a nerve 710 to innervate the muscle and a blood vessel 708 to vascularize the muscle.

Figure 10:
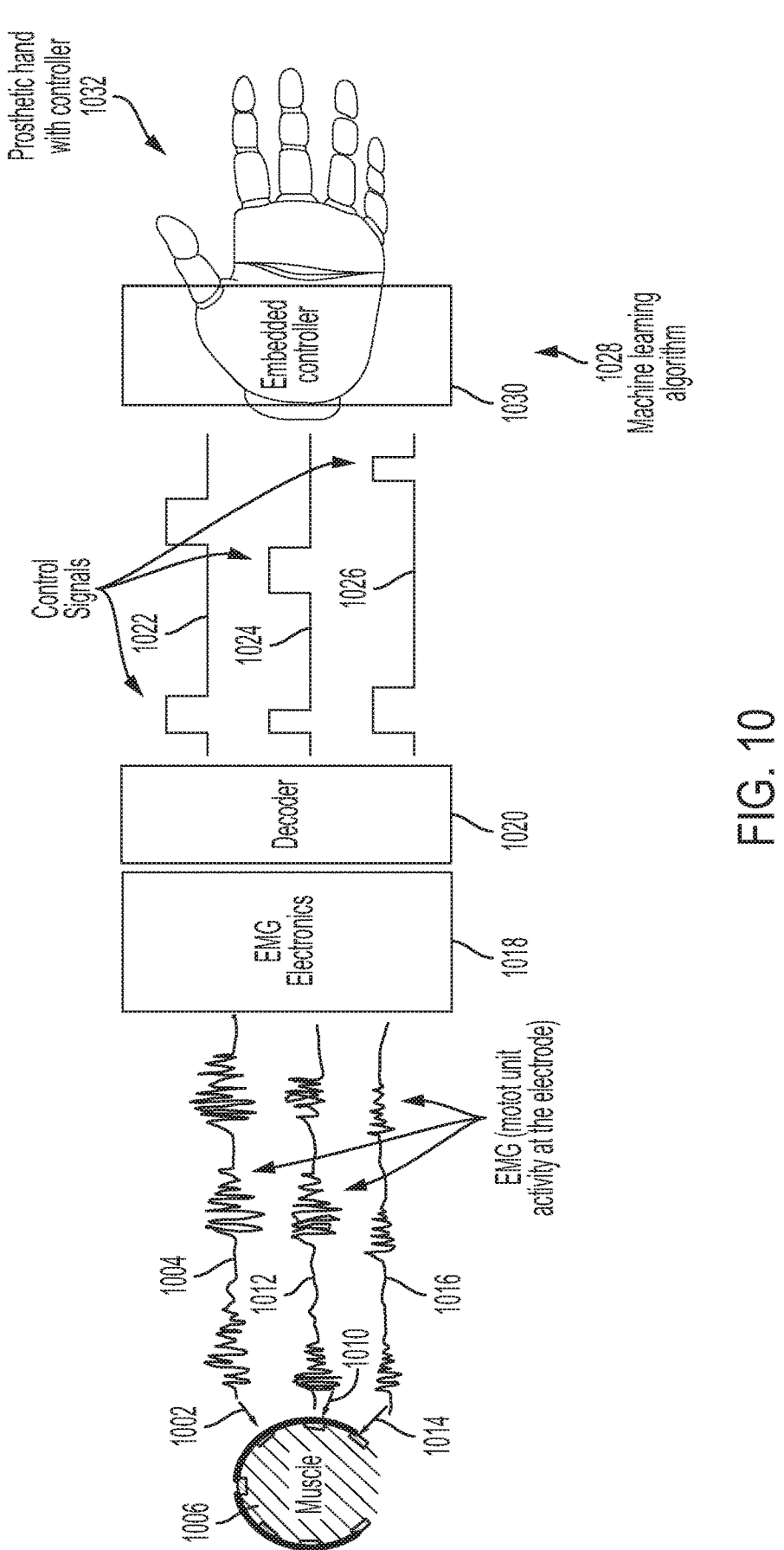
FIG. 10 shows a representation of EMG signals acquired by three separate EMG sensors according to examples of the present disclosure.

FIG. 10 shows a control signal processing based on EMG signals acquired by three separate EMG sensors according to examples of the present disclosure. Sensor 1002 shows EMG 1 1004, which is representative of motor unit activity of muscle 1006 at electrode 1. Sensor 1010 shows EMG 2 1012, which is representative of motor unit activity of muscle 1006 at electrode 2. Sensor 1014 shows EMG 3 1016, which is representative of motor unit activity of muscle 1006 at electrode 3. Each of the EMG 1 1004, EMG 2 1012, and EMG 3 1016 are received by EMG electronics 1018 and decoded by decoder electronics 1020 to produce respective control signals 1022, 1024, and 1026. Control signals 1022, 1024, and 1026 are processed by a machine learning algorithm 1028 to control embedded controller 1030 in prosthetic limb 1032.

Figure 11:
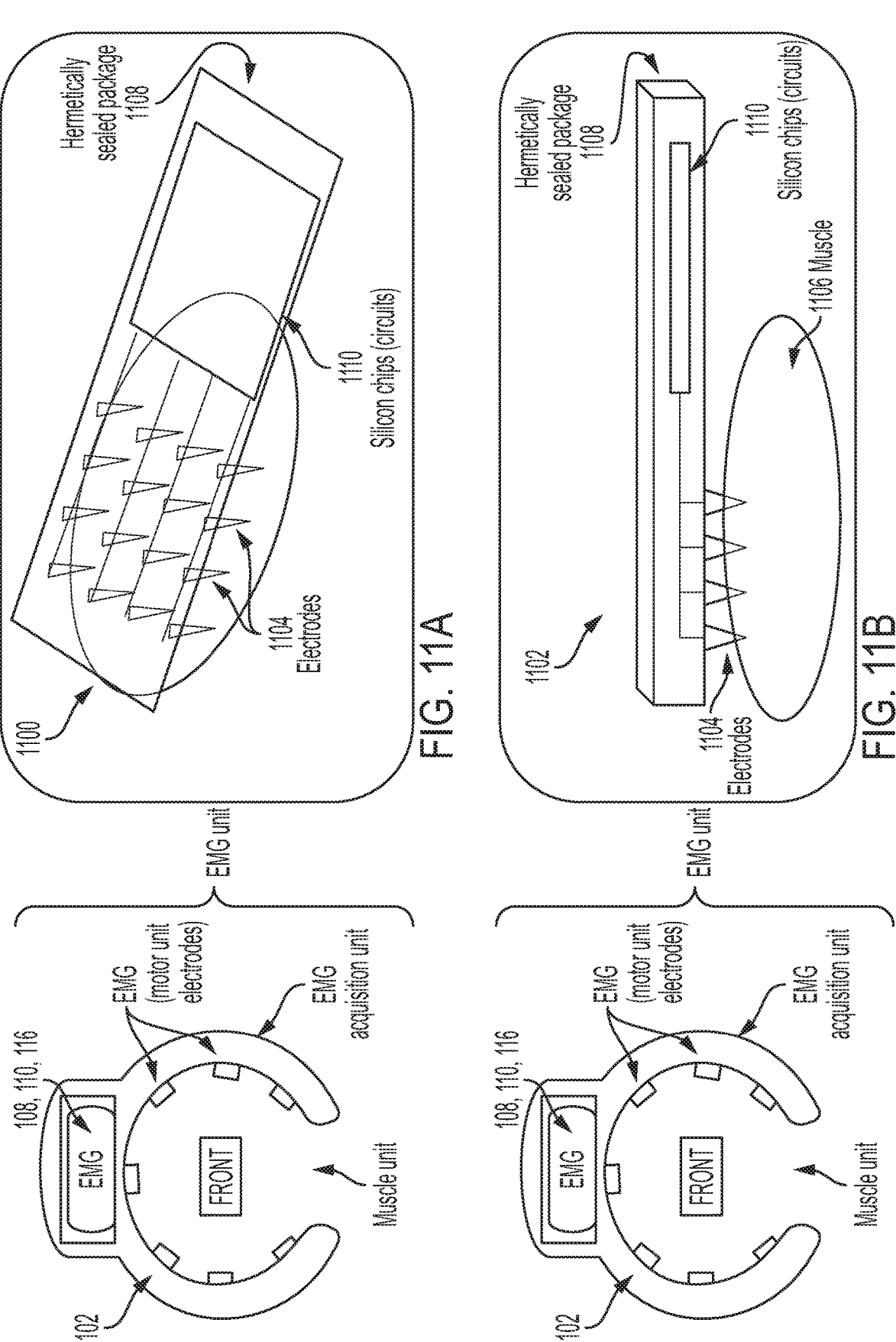
FIG. 11A shows top perspective view 1100 and FIG. 11B shows a side view 1102 representation of EMG unit according to examples of the present disclosure.

FIG. 11A shows top perspective view 1100 and FIG. 11B shows a side view 1102 representation of EMG unit according to examples of the present disclosure. Terminal ends of electrodes 1104 are positioned in physical contact with muscle 1106. Hermetically sealed package 1108 includes electronics 1110 (silicon chips or circuits) that are in electrically contact with the electrodes 1104.

Figure 12:
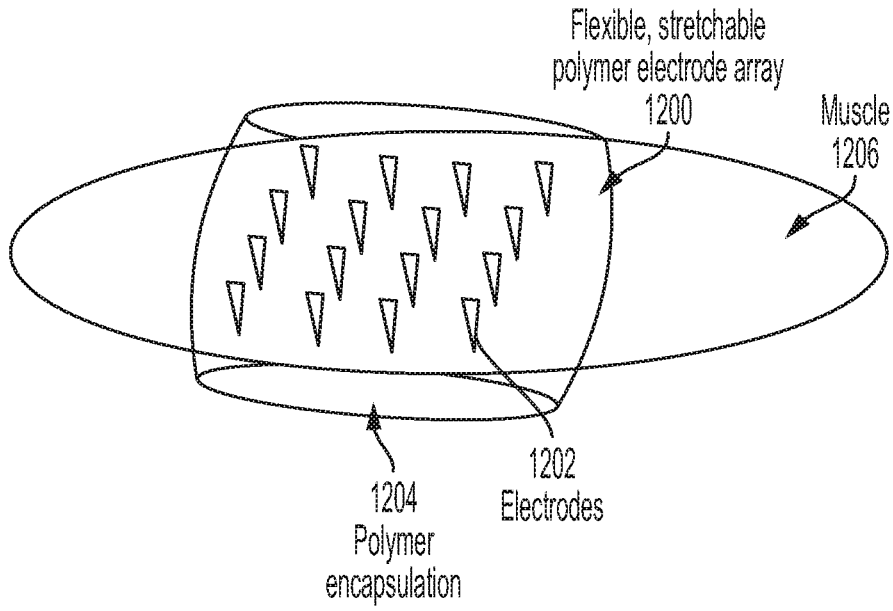
FIG. 12 shows an EMG device with a flexible, stretchable polymer electrode array according to examples of the present disclosure.

FIG. 12 shows an EMG device with a flexible, metal electrode, carbon fibers or fiber-mesh, or stretchable polymer electrode array 1200 according to examples of the present disclosure. Flexible, stretchable polymer electrode array 1200 comprises an array of electrodes 1202 that encapsulated in a polymer material 1204 that are in physical contact with muscle 1206.

Figure 13:
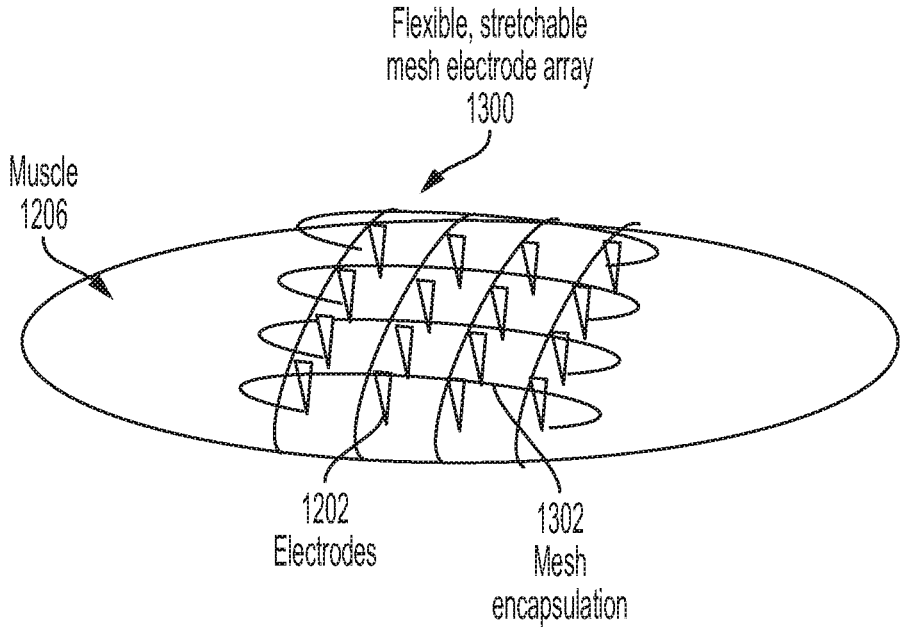
FIG. 13 shows an EMG device with a flexible, stretchable mesh electrode array according to examples of the present disclosure.

FIG. 13 shows an EMG device with a flexible, stretchable mesh electrode array 1300 according to examples of the present disclosure. Flexible, stretchable mesh electrode array 1300 comprises an array of electrodes 1202 that encapsulated in a mesh material 1302 that are in physical contact with muscle 1206.

In accordance with examples of the present disclosure, a flexible wireless device is disclosed that wraps around one or multiple muscles of any kind or size. The flexible wireless device can lay on top of a muscle, wrap around, be sutured, or glued to the entire circumference of an amputation stump. The flexible wireless device can comprise a long sheet of electrodes that is implanted under the skin and on top of the underlying muscle. The sheet of electrodes can conform to any anatomy because it is flexible and/or stretchable. As long as the end of the sheet that contains the wireless powering receiver remains within some distance, on the order of centimeters, to the skin, as for example shown in FIG. 14A, FIG. 14B, FIG. 14C, and FIG. 14D, the rest of the device can configure to whatever the individual user's needs are. Rather than wrapping the flexible sheet of electrodes around a discrete piece of muscle that has been innervated and vascularized, the flexible sheet of electrodes can be implanted and wrapped around one or multiple muscles that may or may not have received any direct manipulation. The state of the muscle is irrelevant in this example. The device comprising the flexible sheet of electrodes can pick up whatever muscle signals are generated within the portion of body it is implanted regardless of whether there has been advanced surgical manipulation (muscle reinnervation) or not. The device can conform to any anatomy that records electrical activity from underlying muscle in the desired fashion.

Figure 14A:
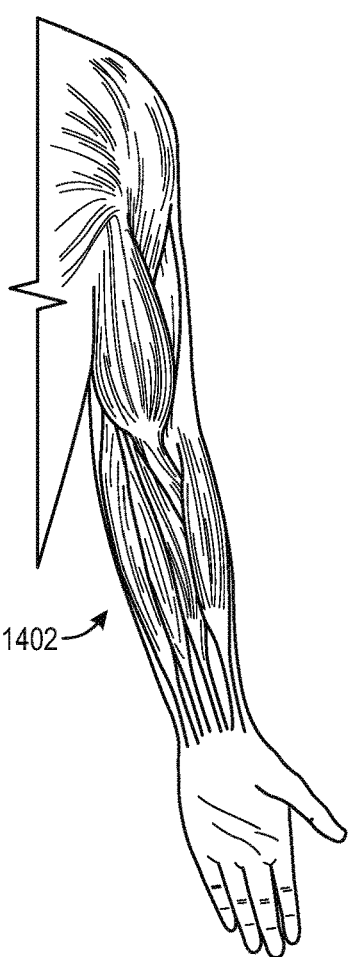
FIG. 14A shows an arm with a dotted line depicting a line of amputation according to examples of the present disclosure.
Figure 14B:
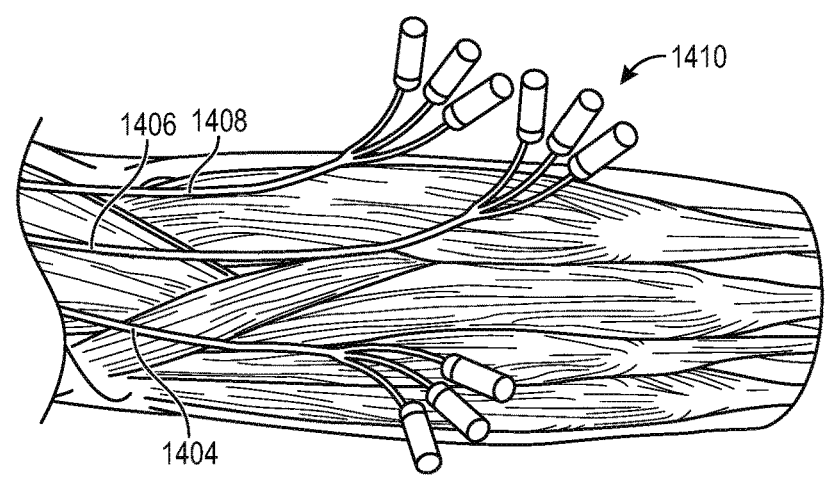
FIG. 14B show a section of the arm of FIG. 14A with the nerve fibers shown with the flexible wireless device wrapped around according to examples of the present disclosure.
Figure 14C:
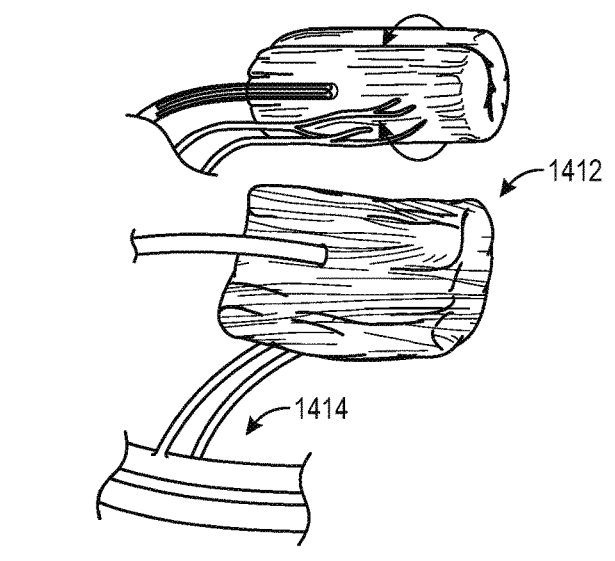
FIG. 14C shows a segment of a muscle fiber that is responsive to activation of nerve fiber and has a connected blood supply according to examples of the present disclosure.
Figure 14D:
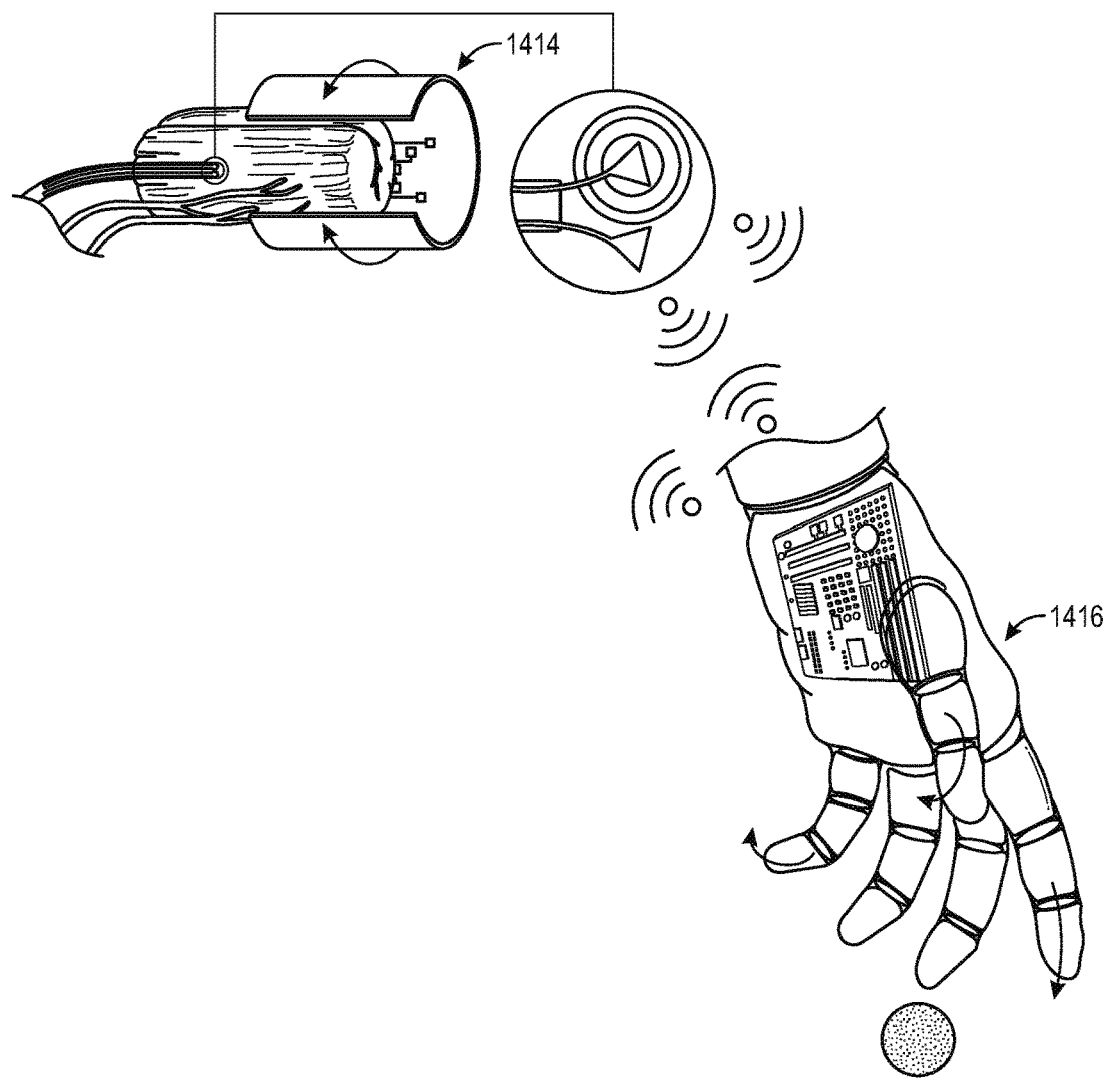
FIG. 14D shows the segment of the muscle fiber of FIG. 14C with the flexible wireless device (e.g., neural wrap) wrapped around the segment according to examples of the present disclosure.

FIG. 14A shows an arm with a dotted line 1402 depicting a line of amputation. FIG. 14B shows the amputation stump of FIG. 14A with the nerve fibers 1404, 1406, and 1408 shown with the flexible wireless device 1410 wrapped around pieces of muscle into which the nerve fibers have been implanted. FIG. 14C shows a segment of a muscle 1412 that is responsive to activation of implanted nerve fiber 1406 and has a connected blood supply 1414. FIG. 14D shows the segment of the muscle of FIG. 14C with the flexible wireless device 1414 (e.g., neural wrap) wrapped around the segment. The segment of muscle 1412 is activated by respective axon signal and subsequentially detected by the flexible wireless device 1414. Wireless control signals are transmitted from the flexible wireless device 1414 to the prosthetic part 1416 or from the flexible wireless device 1502 to an external link 1514 which can then relay signals to the machine of interest (i.e., Prosthesis) 1416.

Figure 18:
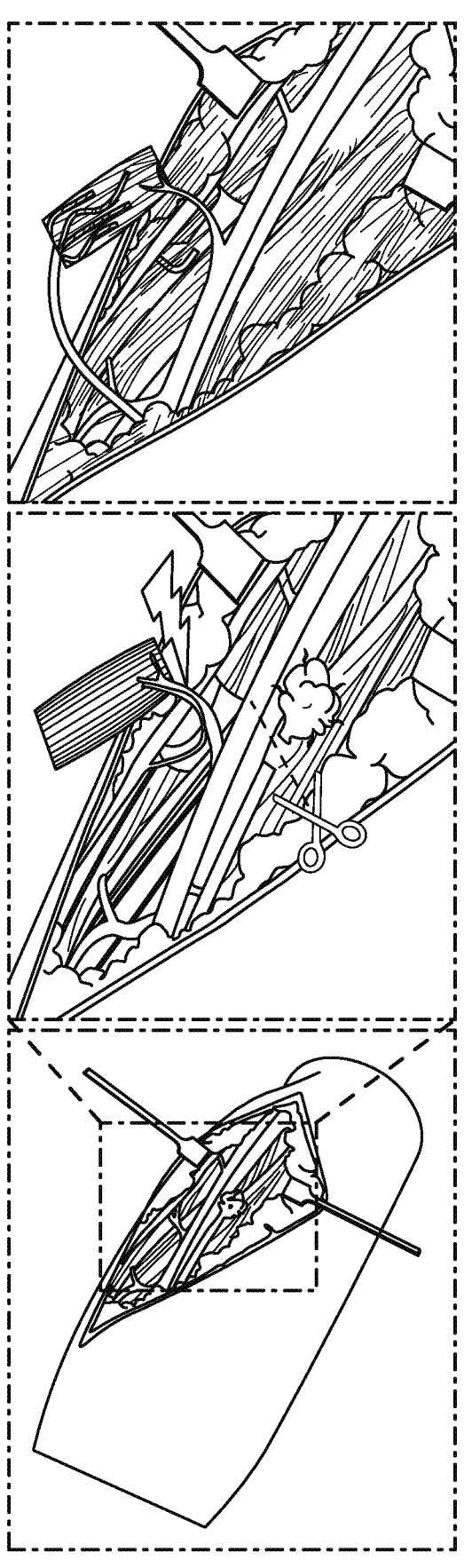
FIG. 18 shows a method for preparing an implantation site according to examples of the present disclosure.

FIG. 18 shows a method for preparing an implantation site according to examples of the present disclosure. The preparing of the implantation site comprises elevating at least a muscle segment of the underlying muscles from surrounding tissues while remaining attached to blood vessels that provide perfusion; identifying nerves supplying the at least the muscle segment with electrical stimulation; dividing the at least muscle segment that is identified to ensure denervation; wrapping a distal end of a proximal stump of a transected nerve or nerve fascicle with at least the muscle segment that is isolated or placing the distal end of the proximal stump of the transected nerve within a portion of the muscle segment and securing the proximal stump with a suture or with fibrin glue.

Figure 15:
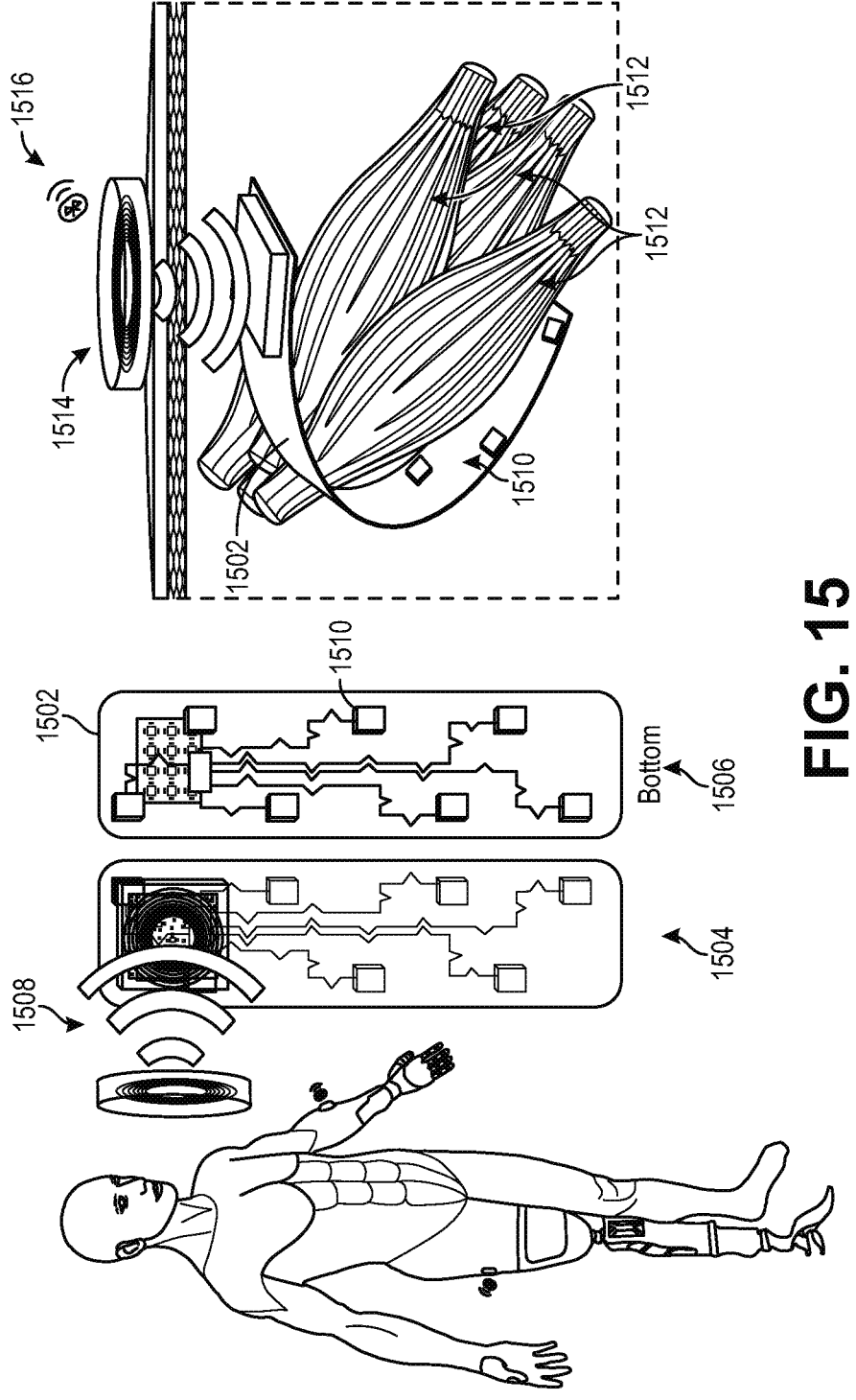
FIG. 15 shows an example use of the flexible wireless device for control of both an upper and a lower limb prosthesis according to examples of the present disclosure.

FIG. 15 shows an example use of the flexible wireless device for both an upper limb and a lower limb prosthesis according to examples of the present disclosure. A top view 1504 and a bottom view 1506 of a flexible wireless device 1502 are shown. The top view 1504 shows an inductive power module 1508 (which can also take the form of some alternative means of power transfer, such as piezo ultrasonic interfacing) and the bottom view 1506 show recording electrodes 1510. The flexible wireless device 1502 surrounds the muscle(s) 1512 where the recording electrodes 1510 detect signals from the muscle 1512. The flexible wireless device 1502 is activated by an external power link 1514 that can contain (but is not limited to) a battery, power transmitter, ASIC, antenna and the flexible wireless device 1502 wirelessly transmits data, via commonly utilized data transfer mechanisms in the form of a wireless data stream 1516 to the external link 1514 or directly to the machine (i.e., Prosthesis, both upper and lower).

In some examples, there can be multiple implants put within the part of the body that is of interest. If one device is not sufficient to cover the desired circumference of the amputation stump, for instance, multiple implants can be implanted to cover the necessary area. Once again, the wireless receiver portion of the implants remain relatively near the skin so that they can be powered or recharged through the skin and overlying tissues. Each device can be powered or recharged separately with its own external link or together via one overlaying coil (or alternative power source, such as ultrasonic transducer).

Figure 16:
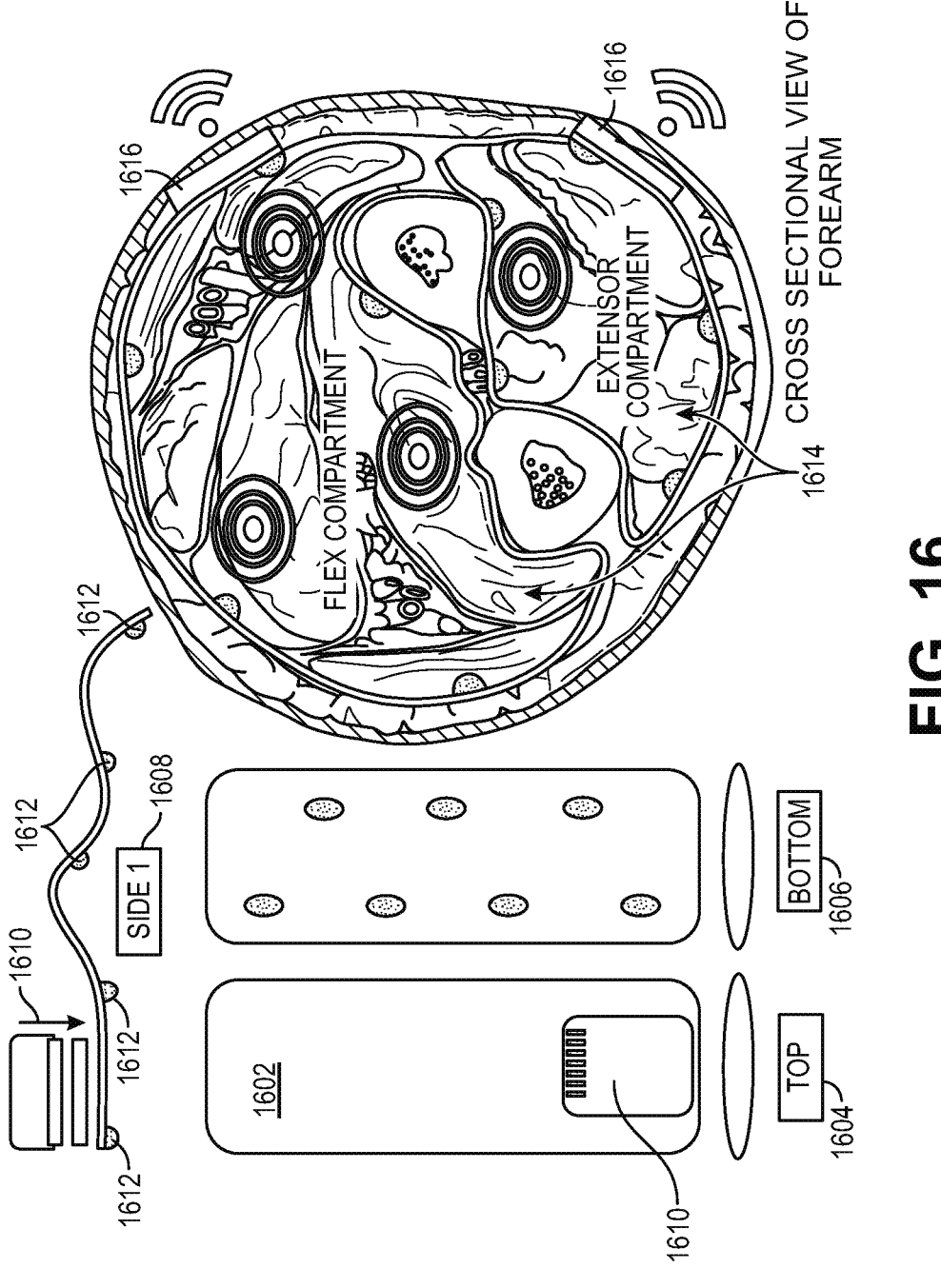
FIG. 16 shows an example use of the flexible wireless device for a hand prosthetic according to examples of the present disclosure.

FIG. 16 shows an example use of the flexible wireless device for a hand prosthetic according to examples of the present disclosure. A top view 1604, a bottom view 1606, a side view 1608 of a flexible wireless device 1602 are shown. The top view 1604 and side view 1608 shows a transceiver and battery module 1610 and the bottom view 1606 and side view 1608 show recording electrodes 1612. The flexible wireless device 1602 surrounds the muscle(s) 1614 where the recording electrodes 1612 detect signals from the muscle(s) 1614. The flexible wireless device 1602 is either actively powered, or recharged, by the transceiver and battery module 1610 and the flexible wireless device 1602 wirelessly transmits data from wireless transmitter module 1616 in the form of a wireless data stream. The flexible wireless device can primarily be continuously powered through transcutaneous inductive means or it can be intermittently recharged through transcutaneous inductive means (or some reasonable alternative power schema). As shown in FIG. 16, there are two separate flexible wireless devices, each surrounding a different cluster of muscles. This is just one non-limiting example. For example, there can be only one flexible wireless device or more than two flexible wireless devices depending on the need, individual anatomy, for example, particular limb and level of amputation, and use cases that apply on a user-by-user basis based on the functional need for limb (or other technology) control.

The flexible wireless device, as disclosed herein, can be implanted in an able bodied (uninjured) individual. The flexible wireless device can be implanted under the skin and connective tissue, around the muscle compartments. The flexible wireless device can then record the signals from the normal muscles below and wirelessly relay them out of the body for any desired purpose. It can be implanted on top of or around any muscle of the body depending on the desired use case.

The flexible wireless device, as disclosed herein, can operate using external powering link/hardware that is held in place via transcutaneous (across the skin) magnetic or radio-frequency (wireless) linkage. The external link can also be held in place via adhesive film, compressive sleeve-like material, clothing, or any other means of fixing an external object to a desired location on the body. The implanted device can wirelessly relay data (via Bluetooth or some other means) to the external power link that is on the surface of the body. The external power link can then wirelessly relay information to any synced device (phone, prosthesis, orthosis, exoskeleton, etc.). The implanted device can also wirelessly relay information directly to a synced device without the powering link as an intermediary. In some examples, some form of data processing can take place within the external powering link prior to subsequent transfer of data to the synced device(s). The implanted system and external power link can switch which device it is synced to, either independently or as a unit, based on the desires of the user.

The implantable device (e.g., flexible wireless device), as disclosed herein, can also impart electrical current into the underlying tissue via the electrodes present on the surface of the device. These electrodes can either be the same electrodes used for recording muscle signals or different electrodes incorporated into the device specifically for stimulating purposes. The purpose of the stimulation is to induce afferent (towards the brain) neural activity in order to treat pain or generate sensations. The excitation of afferent neural activity can be accomplished via ultrasonic means or electrical means. Small ultrasonic transducers can be placed on the surface of the flexible implant, just like electrodes, which can then impart ultrasound energy into the underlying tissue in order to achieve the same effect as electrical stimulation. The electrical/ultrasonic stimulation can be focused or targeted towards discrete locations based on the end-effect that is desired. This can be accomplished via stimulation parameter modulation and spatiotemporal multi-source modulation.

Figure 17:
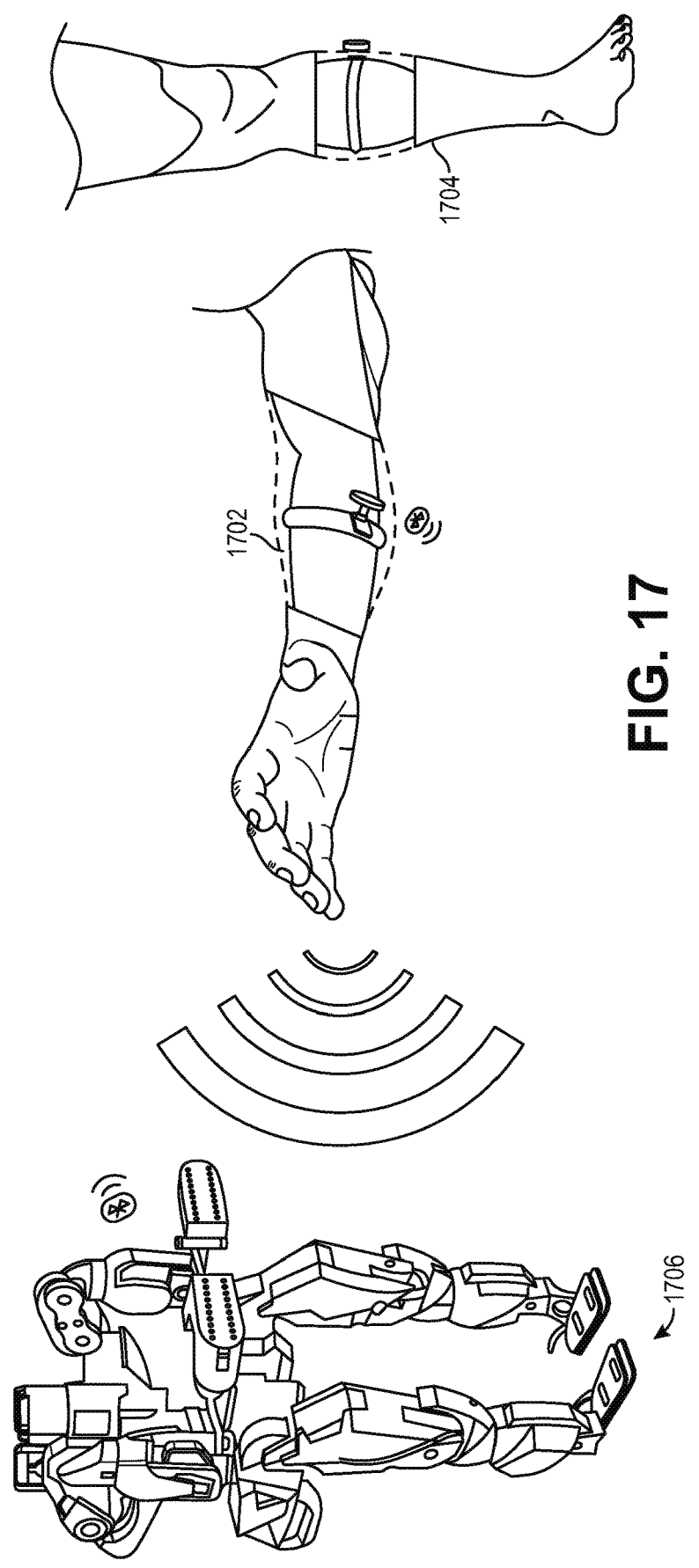
FIG. 17 shows flexible wireless device implanted in an uninjured individual for control of technology, which can be used to wirelessly control a robotic device, such as an exoskeleton, according to examples of the present disclosure.

FIG. 17 shows one or more flexible wireless devices implanted on top of the muscle either within the arm 1702 or the leg 1704 of an able-bodied individual, which can be used to wirelessly control a machine/device such as an exoskeleton 1706.

The foregoing description is illustrative, and variations in configuration and implementation can occur to persons skilled in the art. For instance, the various illustrative logics, logical blocks, modules, and circuits described in connection with the embodiments disclosed herein can be implemented or performed with a general purpose processor, a digital signal processor (DSP), an application specific integrated circuit (ASIC), a field programmable gate array (FPGA), cryptographic co-processor, or other programmable logic device, discrete gate or transistor logic, discrete hardware components, or any combination thereof designed to perform the functions described herein. A general-purpose processor can be a microprocessor, but, in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

What is claimed is:

1. An implantable muscle interface system comprising:
a subdermal substrate comprising:
a first plurality of sensors affixed to subdermal tissue and a second plurality of amplifiers that capture and amplify, respectively, electromyographic (EMG) signals arising from motor units under control of neural signals representative of volitional limb movements; and
a wireless transceiver device electrically connected to the first plurality of sensors that wirelessly transmits signals to an external decoder that produces decoded signals that discriminate motor signals representative of movements of the motor units,
wherein the subdermal substrate at least partially surrounds a muscle from which the EMG signals arise; and
a receiver device that uses the decoded signals for interaction with an external system.

2. The implantable muscle interface system of claim 1, wherein the subdermal substrate is flexible, stretchable, rigid, or semi-rigid.

3. The implantable muscle interface system of claim 1, wherein the receiver device comprises amplifying components, filtering components, wireless communication components, or combinations thereof.

4. The implantable muscle interface system of claim 1, wherein the subdermal substrate, the first plurality of sensors, the second plurality of amplifiers, and the wireless transceiver device are enclosed in a single hermetically sealed container or an encapsulated coating.

5. The implantable muscle interface system of claim 1, further comprising a power source that powers the first plurality of sensors, the second plurality of amplifiers, and the wireless transceiver device.

6. The implantable muscle interface system of claim 5, wherein the subdermal substrate, the first plurality of sensors, the second plurality of amplifiers, the wireless transceiver device, and the power source are enclosed in a single hermetically sealed container or encapsulated coating.

7. The implantable muscle interface system of claim 1, wherein the first plurality of sensors, the second plurality of amplifiers, and the wireless transceiver device are externally powered by an electromagnetic power source, an ultrasonic power source, a piezoelectric power source, or an optical power source.

8. The implantable muscle interface system of claim 1, wherein the signals transmitted by the wireless transceiver device comprise:

analog signals that are multiplexed from channels from the first plurality of sensors or digitized signals generated by digitizing the analog signals that are multiplexed from the channels from the first plurality of sensors and digitized with analog-to-digital converters, or encrypted signals for secure communication.

9. The implantable muscle interface system of claim 1, wherein the subdermal substrate is composed of a biocompatible material comprising polymers, parylene polyimide, plastics, rubbers, silicone, polymeric fiber, silk fibroin, 3D printing polymers, polyimide, Polydimethylsiloxane (PDMS), metals, hydrogels, or acellular scaffolds.

10. The implantable muscle interface system of claim 1, wherein the subdermal substrate is composed of biocompatible polymers with conductive electrodes and conductive traces deposited or embedded therein, comprising biocompatible metals, conductive polymers, electrically conductive carbon-based materials comprising fibers, nanotubes, and graphene, gold, platinum, polypyrrole, Poly (3,4-ethylenedioxythiophene) (PEDOT), poly (3,4-ethylenedioxythiophene) polystyrene sulfonate (PEDOT: PSS), or combinations thereof.

11. The implantable muscle interface system of claim 1, wherein the external system comprises a prosthetic limb, an orthosis, an exoskeleton, a computer, a home appliance, a remote controller, a gaming device, a mobile computing device, an audio device, an augmented reality system, a virtually reality system, or a human augmentation/enhancement device.

12. The implantable muscle interface system of claim 1, wherein the implantable muscle interface system is compatible with target tissue comprising muscles in various biological states including unaltered, vascularized-innervated, vascularized-denervated, devascularized-denervated, devascularized-innervated muscle, or muscle graft including autograft, xenograft, allograft, isograft, cell culture, or a synthetic alternative.

13. The implantable muscle interface system of claim 1, wherein the subdermal substrate comprises a first plurality of electrodes or ultrasonic transducers that provide electrical or ultrasonic stimulation to underlying sensory axons for sensory feedback from prosthetic limbs or exoskeletons.

\* \* \* \* \*